US012758595B2

(12) United States Patent
Song et al.

(10) Patent No.: US 12,758,595 B2
(45) Date of Patent: Oct. 13, 2026

(54) *BACILLUS VELEZENSIS* STRAINS AND COMPOSITION FOR PREVENTING, TREATING, OR IMPROVING TUBERCULOSIS COMPRISING THE SAME

(71) Applicant: SOONCHUNHYANG UNIVERSITY INDUSTRY ACADEMY COOPERATION FOUNDATION, Asan-si (KR)

(72) Inventors: Ho Yeon Song, Cheonan-si (KR); Hoon Hee Seo, Asan-si (KR); Su Kyung Kim, Asan-si (KR)

(73) Assignee: SOONCHUNHYANG UNIVERSITY INDUSTRY ACADEMY COOPERATION FOUNDATION, Asan-si (KR)

( * ) Notice: Subject to any disclaimer, the term of this patent is extended or adjusted under 35 U.S.C. 154(b) by 0 days.

(21) Appl. No.: 18/809,842

(22) Filed: Aug. 20, 2024

(65) Prior Publication Data

US 2025/0127828 A1 Apr. 24, 2025

(30) Foreign Application Priority Data

Oct. 24, 2023 (KR) ........................ 10-2023-0142894

(51) Int. Cl.
*A61K 35/742* (2015.01)
*A61K 45/06* (2006.01)
*A61P 31/06* (2006.01)

(52) U.S. Cl.
CPC ............ *A61K 35/742* (2013.01); *A61K 45/06* (2013.01); *A61P 31/06* (2018.01)

(58) Field of Classification Search
None
See application file for complete search history.

(56) References Cited

U.S. PATENT DOCUMENTS

2010/0008893 A1 1/2010 Rucker

FOREIGN PATENT DOCUMENTS

KR 10-2016-0059474 A 5/2016
KR 10-2021-0046276 A 4/2021

OTHER PUBLICATIONS

Office Action issued in KR 10-2023-0142894; mailed by the Korean Intellectual Property Office on Apr. 29, 2024.
Written Decision On Registration issued in KR 10-2023-0142894; mailed by the Korean Intellectual Property Office on Nov. 21, 2024.
Iñaki Comas et al.; "Out-of-Africa migration and Neolithic co-expansion of *Mycobacterium tuberculosis* with modern humans"; Nat Genet.; Oct. 2013; pp. 1-18.
World Health Organization; "Global tuberculosis report 2021"; Geneva: World Health Organization; 2021; pp. 1-43.
E. Cambau et al.; "Steps toward the discovery of *Mycobacterium tuberculosis* by Robert Koch, 1882"; Clinical Microbiology and Infection and European Society of Clinical Microbiology and Infectious Diseases; Online; Jan. 22, 2014; pp. 196-201.

*Primary Examiner* — Christopher M Babic
(74) *Attorney, Agent, or Firm* — Studebaker Brackett PLLC

(57) ABSTRACT

The present disclosure relates to a novel *Bacillus velezensis* strain and a method for preventing, treating, or improving tuberculosis comprising the same. More specifically, the present disclosure relates to a *Bacillus velezensis* PMC 206 strain extracted from vinegar and a use thereof, for example, an antibacterial composition having antibacterial activity against bacteria belonging to the genus *Mycobacterium*, a pharmaceutical composition or food composition for improving, treating, or preventing tuberculosis having anti-bacterial activity against bacteria belonging to the genus *Mycobacterium.*

7 Claims, 8 Drawing Sheets

Specification includes a Sequence Listing.

FIG. 1A
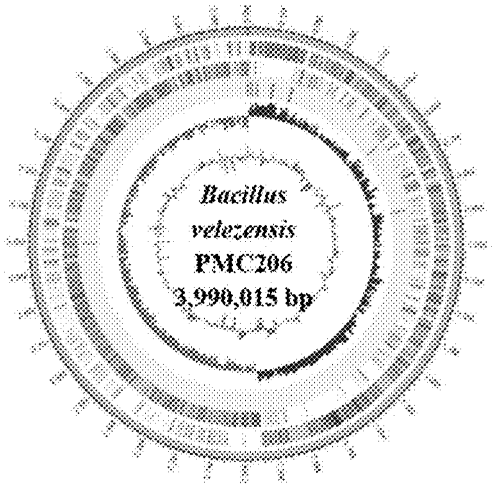
FIG. 1B
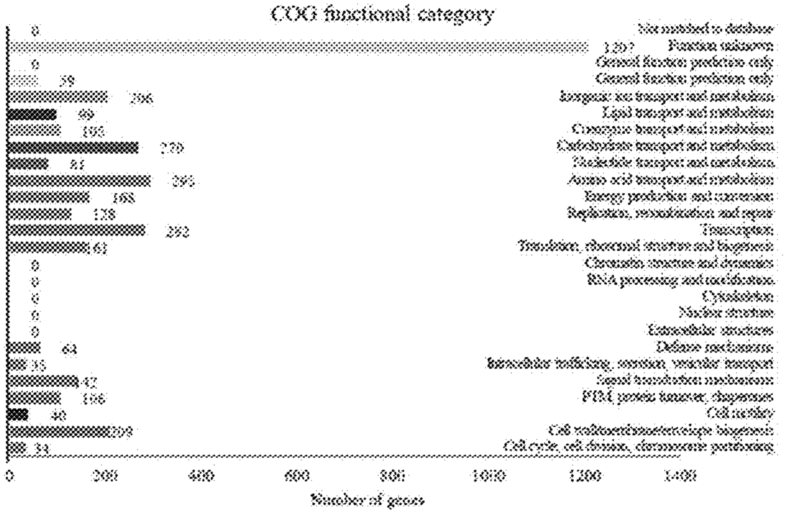
FIG. 1C
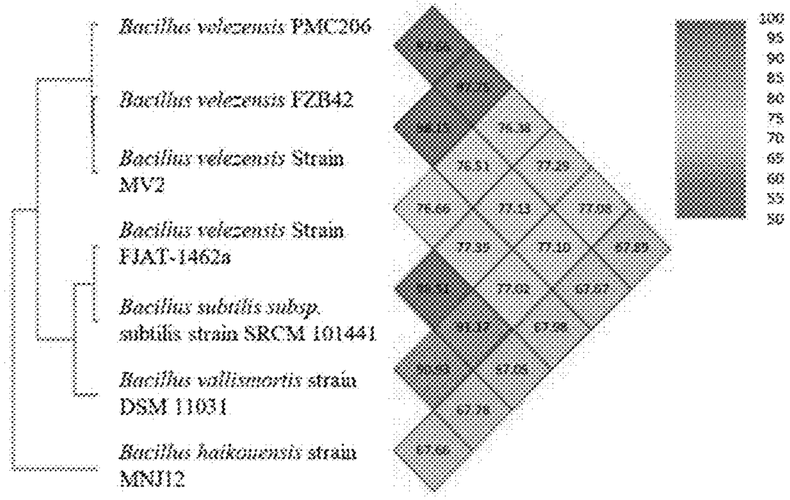
FIG. 1D
| Strain | PMC206 | ATR2 | Yao | UD6-2 | RC116 |
|---|---|---|---|---|---|
| Sources | Korean Gochang vinegar | Soil | Capsicum annuum | Salted fermented fish | Tomato |
| Genome size (bp) | 3,990,015 | 4,006,746 | 3,951,864 | 3,951,373 | 4,020,633 |
| G+C content (%) | 46.6 | 46.3 | 46.6 | 45.2 | 46.1 |
| Predicted CDS | 3,841 | 3,815 | 3,821 | 3,865 | 3,913 |
| Number of rRNA genes | 32 | 21 | 27 | 6 | 28 |
| Number of tRNA genes | 0 | 0 | 0 | 1 | 0 |

H37Rv strain
CFU/ml (log10)
Control (Drug free)
RIF (µg/ml)
INH (µg/ml)
PMC206 (1×10⁶ CFU/ml)

XDR strain
CFU/ml (log10)
Control (Drug free)
RIF (µg/ml)
INH (µg/ml)
PMC206 (1×10⁶ CFU/ml)

H37Rv strain
CFU/ml (log10)
Control (Drug free)
RIF (µg/ml)
INH (µg/ml)
RIF 0.1 µg/ml + PMC206 (1×10⁶ CFU/ml)

Cell cytotoxicity
Viable cell density (× 10⁴ cells/ml)
Control (Drug free)
PMC206 concentration (1×10⁶ CFU/ml)

*BACILLUS VELEZENSIS* STRAINS AND COMPOSITION FOR PREVENTING, TREATING, OR IMPROVING TUBERCULOSIS COMPRISING THE SAME

CROSS-REFERENCE TO RELATED APPLICATION

This application claims the benefit of priority from the prior Korean Patent Application No. 10-2023-0142894, filed on Oct. 24, 2023, the disclosures of which are incorporated herein by reference in its entirety.

REFERENCE TO AN ELECTRONIC SEQUENCE LISTING

The entire contents of the electronic file identified by its name Sequence Listing.xml, creation date Apr. 2, 2026, and size 7,024 bytes are incorporated herein by reference. Neither the presence nor absence of information that is not required under the sequence rules will create a presumption that such information is necessary to satisfy any of the requirements of 35 U.S.C. 112. Further, the grant of a patent on an application that is subject to the sequence rules (37 CFR 1.831 et seq.) constitutes a presumption that the granted patent complies with the requirements of these rules.

TECHNICAL FIELD

The present disclosure relates to a novel *Bacillus* velezensis strain and a method for preventing, treating, or improving tuberculosis including the same. More specifically, the present disclosure relates to a *Bacillus* velezensis PMC 206 strain extracted from vinegar and a use thereof, for example, an antibacterial composition having antibacterial activity against bacteria belonging to the genus *Mycobacterium*, and a pharmaceutical composition or food composition for improving, treating, or preventing tuberculosis having antibacterial activity against bacteria belonging to the genus *Mycobacterium.*

BACKGROUND

Tuberculosis is an infectious disease caused by *Mycobacterium tuberculosis*. Tuberculosis remains a major global public health problem, causing about 1.8 million deaths each year. Drug-resistant *Mycobacterium tuberculosis*, including multi-drug resistant (MDR) tuberculosis, broad-spectrum resistant (XDR) tuberculosis, and totally drug resistant (TDR) tuberculosis, continues to pose a threat to public health. Conventional antibiotics are less effective when they are used to treat antibiotic-resistant tuberculosis. Additionally, in the case of existing therapeutic agents, side effects due to long-term high doses of the drug cause serious problems.

Accordingly, in order to overcome these problems, there is an urgent need to develop a new type of anti-tuberculosis drug that is different from the existing compound-based antibiotics.

PRIOR ART DOCUMENTS

Non-patent Document 1. Comas I, Coscolla M, Luo T, et al. Out-of-Africa migration and Neolithic coexpansion of *Mycobacterium tuberculosis* with modern humans. Nat Genet. 2013 October; 45(10):1176-82.

Non-patent Document 2. WHO. Global tuberculosis report 2021. Geneva: World Health Organization; 2021.

Non-patent Document 3. Cambau E, Drancourt M. Steps towards the discovery of *Mycobacterium tuberculosis* by Robert Koch, 1882. Clin Microbiol Infec. 2014 March; 20(3):196-201.

Technical Problem

An object of the present disclosure is to provide a *Bacillus velezensis* PMC 206 strain.

Another object of the present disclosure is to provide an antibacterial composition including a *Bacillus velezensis* PMC 206 strain.

Still another object of the present disclosure is to provide a composition for preventing, treating, or improving tuberculosis including a *Bacillus velezensis* PMC 206 strain.

Technical Solution

According to the first exemplary embodiment, the present disclosure provides a *Bacillus velezensis* PMC 206 strain or a culture thereof, which has antibacterial activity against bacteria belonging to the genus *Mycobacterium*.

According to the present disclosure, the *Bacillus velezensis* PMC 206 strain may be extracted from vinegar. For example, *Bacillus velezensis* PMC 206 strain is assigned Accession No. KCTC 15187BP. *Bacillus velezensis* PMC 206 strain was deposited under the Budapest Treaty with the Korean Collection for Type Cultures (KCTC), located in Korea Research Institute of Bioscience and Biotechnology 181, Ipsin-gil, Jeongeup-si, Jeollabuk-do 56212, Republic of Korea, under Accession No. KCTC 15187BP, on Nov. 9, 2022. All restrictions imposed by the depositor on the availability to the public of the deposited biological material will be irrevocably removed upon the granting of the patent.

According to the present disclosure, the bacteria belonging to the genus *Mycobacterium* may be one or more selected from the group consisting of *M. abscessus, M. africanum, M. asiaticum, M. avium complex* (MAC), *M. bovis, M. chelonae, M. fortuitum, M. gordonae, M. haemophiluscellulare, M. kansasii, M. lentiflavum, M. leprae, M. malmoense, M. marinum, M. microti, M. phlei, M. scrofulaceum, M. smegmatis, M. triplex, M. tuberculosis, M. ulcerans*, and *M. xenopi.*

According to the second exemplary embodiment, the present disclosure provides an antibacterial composition having antibacterial activity against bacteria belonging to the genus *Mycobacterium*, which includes a *Bacillus velezensis* PMC 206 strain or a culture thereof.

According to the present disclosure, the *Bacillus velezensis* PMC 206 strain may be extracted from vinegar. For example, *Bacillus velezensis* PMC 206 strain is assigned Accession No. KCTC 15187BP.

According to the present disclosure, the bacteria belonging to the genus *Mycobacterium* may be one or more selected from the group consisting of *M. abscessus, M. africanum, M. asiaticum, M. avium complex* (MAC), *M. bovis, M. chelonae, M. fortuitum, M. gordonae, M. haemophiluscellulare, M. kansasii, M. lentiflavum, M. leprae, M. malmoense, M. marinum, M. microti, M. phlei, M. scrofulaceum, M. smegmatis, M. triplex, M. tuberculosis, M. ulcerans*, and *M. xenopi.*

In the present disclosure, the antibacterial composition may be used in living organisms.

In the present disclosure, the antibacterial composition may be used in an in vitro environment.

According to the third exemplary embodiment, the present disclosure provides a pharmaceutical composition for treating or preventing tuberculosis having antibacterial activity against bacteria belonging to the genus *Mycobacterium*, which includes a *Bacillus velezensis* PMC 206 strain or a culture thereof as an active ingredient.

According to the present disclosure, the *Bacillus velezensis* PMC 206 strain may be extracted from vinegar. For example, *Bacillus velezensis* PMC 206 strain is assigned Accession No. KCTC 15187BP.

According to the present disclosure, the bacteria belonging to the genus *Mycobacterium* may be one or more selected from the group consisting of *M. abscessus, M. africanum, M. asiaticum, M. avium complex* (MAC), *M. bovis, M. chelonae, M. fortuitum, M. gordonae, M. haemophiluscellulare, M. kansasii, M. lentiflavum, M. leprae, M. malmoense, M. marinum, M. microti, M. phlei, M. scrofulaceum, M. smegmatis, M. triplex, M. tuberculosis, M. ulcerans*, and *M. xenopi.*

In the present disclosure, the tuberculosis may include one or more selected from the group consisting of ocular tuberculosis, skin tuberculosis, adrenal tuberculosis, renal tuberculosis, epididymal tuberculosis, lymphatic tuberculosis, laryngeal tuberculosis, middle ear tuberculosis, intestinal tuberculosis, multidrug-resistant tuberculosis, pulmonary tuberculosis, biliary tuberculosis, bone tuberculosis, throat tuberculosis, breast tuberculosis, and spinal tuberculosis.

In the present disclosure, the tuberculosis may be latent tuberculosis.

In the present disclosure, the pharmaceutical composition may further include at least one selected from the group consisting of rifampicin, rifapentine, isoniazid, pyrazinamide, ethambutol, streptomycin, fluoroquinolone, kanamycin, cycloserine, prothionamide, levofloxacin, moxifloxacin, ofloxacin, rifabutin, capeomycin, amikacin, ciprofloxacin, protionamide, ethionamide, cycloserine, thioacetazone, clofazimine, amoxicillin/clavulanate, a derivative of dianomidiphenylsulphone, clarithromycin, azithromycin, and linezolid.

According to the fourth exemplary embodiment, the present disclosure provides a food composition for preventing or improving tuberculosis having antibacterial activity against bacteria belonging to the genus *Mycobacterium*, which includes the *Bacillus velezensis* PMC 206 strain or a culture thereof as an active ingredient.

According to the present disclosure, the *Bacillus velezensis* PMC 206 strain may be extracted from vinegar. For example, *Bacillus velezensis* PMC 206 strain is assigned Accession No. KCTC 15187BP.

According to the present disclosure, the bacteria belonging to the genus *Mycobacterium* may be one or more selected from the group consisting of *M. abscessus, M. africanum, M. asiaticum, M. avium complex* (MAC), *M. bovis, M. chelonae, M. fortuitum, M. gordonae, M. haemophiluscellulare, M. kansasii, M. lentiflavum, M. leprae, M. malmoense, M. marinum, M. microti, M. phlei, M. scrofulaceum, M. smegmatis, M. triplex, M. tuberculosis, M. ulcerans*, and *M. xenopi.*

In the present disclosure, the tuberculosis may include one or more selected from the group consisting of ocular tuberculosis, skin tuberculosis, adrenal tuberculosis, renal tuberculosis, epididymal tuberculosis, lymphatic tuberculosis, laryngeal tuberculosis, middle ear tuberculosis, intestinal tuberculosis, multidrug-resistant tuberculosis, pulmonary tuberculosis, biliary tuberculosis, bone tuberculosis, throat tuberculosis, breast tuberculosis, and spinal tuberculosis.

In the present disclosure, the tuberculosis may be extensive drug-resistance (XRD) tuberculosis.

Advantageous Effects

The present disclosure provides a *Bacillus velezensis* PMC 206 strain which has antibacterial activity. More specifically, the strain has antibacterial activity against *Mycobacterium tuberculosis*. Therefore, the strain may be used for treating, preventing, or improving tuberculosis.

In particular, the strain has the advantage in that it has no side effects due to drug resistance and long-term high-dose drug treatment, compared to compound-based drug treatment.

BRIEF DESCRIPTION OF THE DRAWINGS

FIGS. 1A-1D shows the genetic characteristics of a *Bacillus velegensis* PMC 206 strain according to the present disclosure.

DETAILED DESCRIPTION

Figures 2A, 2B, 2C, 2D:
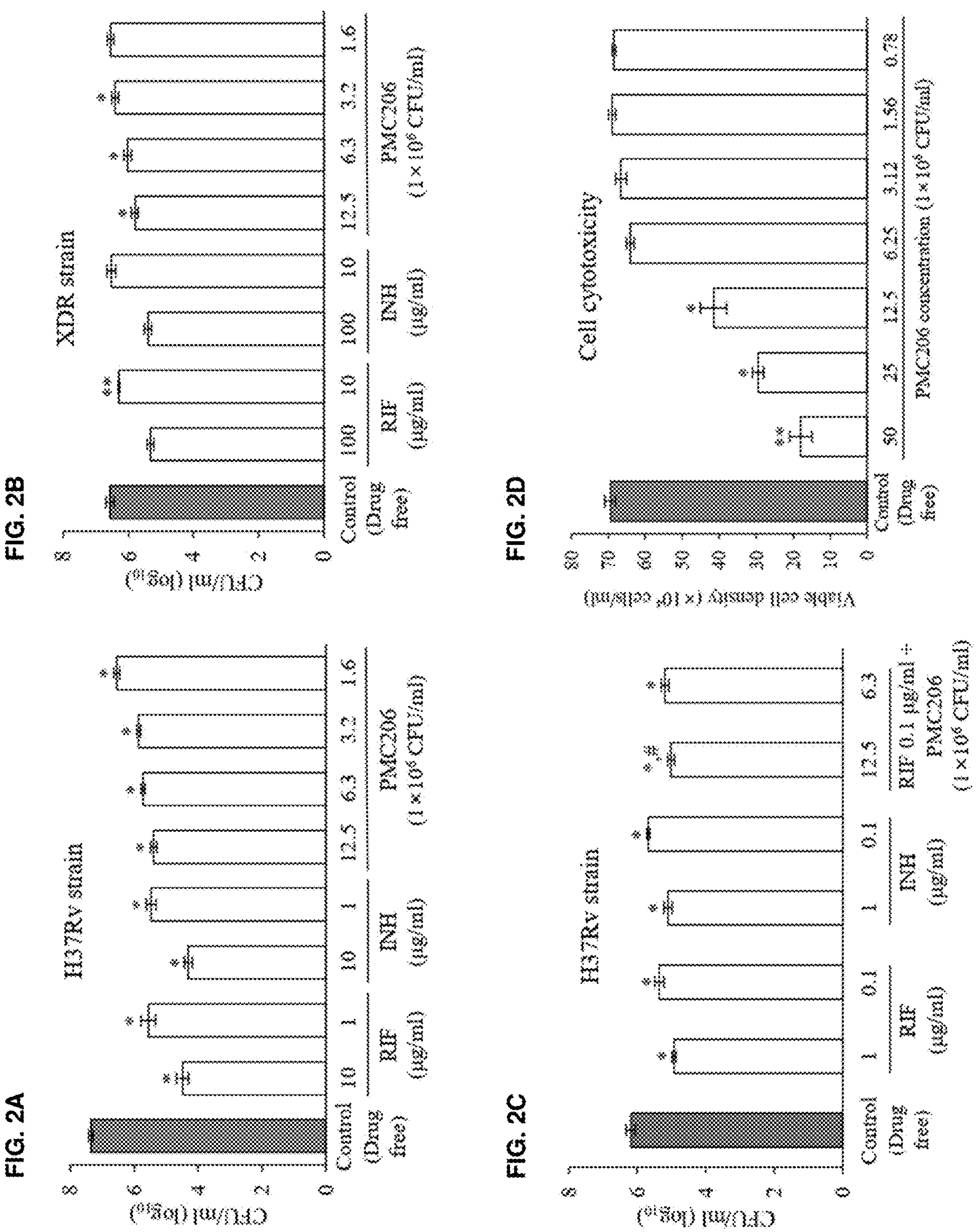
FIGS. 2A-2D shows the anti-tuberculosis effect and cytotoxicity of the *Bacillus velegensis* PMC 206 strain according to the present disclosure against macrophages infected with *M. tuberculosis.*

Unless otherwise defined, all technical and scientific terms used herein have the same meaning as commonly understood by those skilled in the technical field to which the present disclosure pertains. All publications, patents, and other references mentioned herein are incorporated by reference in their entirety.

As used herein, the term "extensive drug-resistance (XRD)" refers to drug resistance, and particularly, resistance to a wide range of drugs.

As used herein, the term "antibacterial" refers to killing microorganisms or inhibiting the growth of microorganisms. In one embodiment, as used herein, the term may be used to mean killing a specific microorganism or inhibiting the growth of a specific microorganism. In a specific embodiment, as used herein, the term may be used to mean killing bacteria belonging to the genus *Mycobacterium* or inhibiting its growth. In a more specific embodiment, as used herein, the term may be used to mean killing one or more bacteria selected from the group consisting of *M. abscessus, M. africanum, M. asiaticum, M. avium complex* (MAC), *M. bovis, M. chelonae, M. fortuitum, M. gordonae, M. haemophiluscellulare, M. kansasii, M. lentiflavum, M. leprae, M. malmoense, M. marinum, M. microti, M. phlei, M. scrofulaceum, M. smegmatis, M. triplex, M. tuberculosis, M. ulcerans*, and *M. xenopi*, or inhibiting their growth.

As used herein, the term "prevention" refers to any action without limitation that blocks the symptoms caused by tuberculosis or inhibits or delays the onset of the symptoms by using the composition of the present disclosure, which includes a *Bacillus velezensis* PMC 206 strain as an active ingredient.

As used herein, the terms "improvement" and "treatment" refer to any action without limitation that improves the symptoms caused by tuberculosis or becomes beneficial, by using the composition of the present disclosure, which includes a *Bacillus velezensis* PMC 206 strain as an active ingredient.

Hereinafter, the specific details of the present disclosure are described.

I. Strains

Strains Obtained from Fermented Foods

The present disclosure intends to provide a *Bacillus velezensis* PMC 206 strain. The *Bacillus velezensis* PMC 206 strain may be obtained from fermented foods. In an exemplary embodiment, the *Bacillus velezensis* PMC 206 strain may be extracted from vinegar. For example, the *Bacillus velezensis* PMC 206 strain is assigned Accession No. KCTC 15187BP. 16S rRNA sequence of KCTC15187BP is SEQ ID NO: 1.

Non-Cytotoxic Strains

Antibacterial Composition Used in In Vivo and In Vitro Environments

The present disclosure intends to provide an antibacterial composition including a *Bacillus velezensis* PMC 206 strain. Since the strain is non-cytotoxic, it may be included in compositions which are used in vivo and in vitro.

The antibacterial composition may be an antibacterial composition administered to a living body. In particular, the living organism refers to a living individual, and the individual includes mammals including humans. That is, the present disclosure provides, in an embodiment, an antibacterial composition which has antibacterial activity against undesired microorganisms present in mammals including humans. In a specific embodiment, the present disclosure provides an antibacterial composition having antibacterial activity against pathogenic bacteria present in mammals including humans.

The antibacterial composition including the *Bacillus velezensis* PMC 206 strain may be an antibacterial composition that has antibacterial activity against undesired microorganisms existing in an in vitro environment. In a specific embodiment, the antibacterial composition including the *Bacillus velezensis* PMC 206 strain provides an antibacterial composition having antibacterial activity against pathogenic bacteria present in an in vitro environment. In particular, the term "in vitro environment" is an exemplary embodiment and may refer to the surface of a material that needs to be washed. In particular, the term "washing" may refer to removal of undesired microorganisms. In particular, the term "removal" may refer to killing some bacteria, inhibiting the growth of bacteria, or reducing the number of bacteria.

The surface of the material may include the surface of household goods including furniture, dishware, home appliances, etc., but is not limited thereto and includes all surfaces of materials that need to be washed. That is, the present disclosure provides an antibacterial composition having antibacterial activity against pathogenic microorganisms existing in an in vitro environment.

Antibacterial Methods Used in In Vivo and In Vitro Environments

The present disclosure also intends to provide an antibacterial method using an antibacterial composition including a *Bacillus velezensis* PMC 206 strain.

The antibacterial method may include administering the antibacterial composition to a living body. The living organism refers to a living individual, and the individual includes mammals including humans. That is, the present disclosure provides an antibacterial method which includes administering the composition to mammals including humans.

The antibacterial method may also include treating the antibacterial composition in vitro. The in vitro refers to the surface of a material that needs to be washed, and the present disclosure provides an antibacterial method for treating the surface of a material that needs to be washed with the antibacterial composition.

Types of Strains Included in Composition

The present disclosure provides a *Bacillus velezensis* PMC 206 strain, an antibacterial composition including the strain, and a pharmaceutical composition and a food composition for treating, preventing, and improving tuberculosis and inflammatory diseases including the strain. In particular, in one embodiment, the composition may include the *Bacillus velezensis* PMC 206 strain in the form of live cells, dead cells, or a culture thereof. As used herein, the culture may be a culture including the *Bacillus velezensis* PMC 206 strain, or it may include its lysate, a supernatant or pellet after centrifugation, a concentrate, a dried material, etc.

II. Antibacterial Composition

The present disclosure provides an antibacterial composition including a *Bacillus velezensis* PMC 206 strain. The antibacterial composition may have antibacterial activity against bacteria belonging to the genus *Mycobacterium*. In a specific embodiment, the antibacterial composition may have antibacterial activity against one or more bacteria selected from the group consisting of *M. abscessus, M. africanum, M. asiaticum, M. avium complex* (MAC), *M. bovis, M. chelonae, M. fortuitum, M. gordonae, M. haemophiluscellulare, M. kansasii, M. lentiflavum, M. leprae, M. malmoense, M. marinum, M. microti, M. phlei, M. scrofulaceum, M. smegmatis, M. triplex, M. tuberculosis, M. ulcerans*, and *M. xenopi*. In a more specific embodiment, the antibacterial composition may have antibacterial activity against *M. tuberculosis*.

III. Composition for Improving, Treating, or Preventing Tuberculosis

Pharmaceutical Composition for Treating or Preventing Tuberculosis

The present disclosure provides a pharmaceutical composition for treating or preventing tuberculosis including a *Bacillus velezensis* PMC 206 strain.

As used herein, the term "tuberculosis" refers to an infectious disease transmitted by *Mycobacterium tuberculosis*. For example, the tuberculosis may be one or more selected from the group consisting of ocular tuberculosis, skin tuberculosis, adrenal tuberculosis, renal tuberculosis, epididymal tuberculosis, lymphatic tuberculosis, laryngeal tuberculosis, middle ear tuberculosis, intestinal tuberculosis, multidrug-resistant tuberculosis, pulmonary tuberculosis, biliary tuberculosis, bone tuberculosis, throat tuberculosis, lung deficiency syndrome, breast tuberculosis, and spinal tuberculosis, but is not limited thereto.

In a pharmaceutical composition for treating or preventing tuberculosis according to the present disclosure, the pharmaceutical composition may further include a carrier. For example, the pharmaceutically acceptable carrier may be one which is commonly used in preparation, and may include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, etc., but is not limited thereto. The pharmaceutical composition may further include a lubricant, a wetting agent, a sweetener, a flavoring agent, an emulsifier, a suspending agent, a preservative, etc., in addition to the ingredients described above. Suitable pharmaceutically acceptable carriers and formulations are described in detail in Remington's Pharmaceutical Sciences (19th ed., 1995).

In the pharmaceutical composition for treating or preventing tuberculosis according to the present disclosure, the pharmaceutical composition may be prepared by mixing one or more diluents or excipients such as such as fillers, extenders, binders, wetting agents, disintegrants, and surfactants commonly used in this technical field. For example, solid preparations for oral administration include tablets, pills, powders, granules, capsules, troches, etc. These solid preparations are prepared by mixing the strain of the present disclosure or a culture thereof with at least one excipient, such as starch, calcium carbonate, sucrose, lactose, or gelatin. Additionally, in addition to simple excipients, lubricants such as magnesium styrate talc may also be used. Liquid preparations for oral administration may include suspensions, oral solutions, emulsions, syrups, etc., for example, may include wetting agents, sweeteners, fragrances, preservatives, etc. may be included. Preparations for parenteral administration include sterilized aqueous solutions, non-aqueous solutions, suspensions, emulsions, lyophilized preparations, suppositories, etc. Non-aqueous solvents and suspensions may include propylene glycol, polyethylene glycol, vegetable oil (e.g., olive oil), and injectable ester (e.g., ethyl oleate), etc. As a base for suppositories, witepsol, macrogol, tween 61, cacao butter, laurinum, glycerol, gelatin, etc. may be used.

In the pharmaceutical composition for treating or preventing tuberculosis according to the present disclosure, the pharmaceutical composition may further include materials that can improve the effects of preventing or treating diseases. For example, the pharmaceutical composition may further include at least one selected from the group consisting of rifampicin, rifapentine, isoniazid, pyrazinamide, ethambutol, streptomycin, fluoroquinolone, kanamycin, cycloserine, prothionamide, levofloxacin, moxifloxacin, ofloxacin, rifabutin, capeomycin, amikacin, ciprofloxacin, protionamide, ethionamide, thioacetazone, clofazimine, amoxicillin/clavulanate, a derivative of dianomidiphenylsulphone, clarithromycin, azithromycin, and linezolid. According to an exemplary embodiment, the pharmaceutical composition may further include rifampicin in the *Bacillus velezensis* PMC 206 strain.

Method for Treating Tuberculosis

The present disclosure provides a method for treating tuberculosis which includes administering, to an individual, a composition including a *Bacillus velezensis* PMC 206 strain. In particular, the individual may refer to a mammal including humans.

In the method for treating tuberculosis according to the present disclosure, the composition may be administered orally or parenterally (e.g., intravenously, subcutaneously, intraperitoneally, or topically) depending on the desired method, and the dose varies depending on the patient's condition and weight, degree of disease, drug type, and route and time of administration, but may be appropriately selected by those skilled in the art.

In the method for treating tuberculosis according to the present disclosure, the composition is administered in a pharmaceutically effective amount. The "pharmaceutically effective amount" refers to an amount sufficient to treat a disease with a reasonable benefit/risk ratio applicable to medical treatment, and the effective dose level may be determined depending on factors including the type and severity of the patient's disease, drug activity, sensitivity to the drug, time of administration, route of administration and excretion rate, duration of treatment, drugs used concurrently, and other factors well known in the field of medicine. The composition of the present disclosure may be administered as an individual treatment or in combination with other treatments, may be administered sequentially or simultaneously with conventional treatments, and may be administered once or multiple times. Considering all of the factors described above, it is important to administer an amount that may achieve a maximum effect with a minimum amount without side effects, and this may easily be determined by those skilled in the art. In particular, the composition of the present disclosure and rifampicin may be administered together. When rifampicin is administered together, the effects of prevention and treatment of the disease caused by the composition of the present disclosure may be improved. Specifically, the effective amount of the composition according to the present disclosure may vary depending on the patient's age, sex, and body weight, generally 0.1 mg to 100 mg, preferably 0.5 mg to 10 mg per kg of body weight, and may be administered daily or every other day, or may be administered in 1 to 3 divided doses daily. However, since the dose may increase or decrease depending on the route of administration, severity of obesity, sex, body weight, age, etc., the dose does not limit the scope of the present disclosure in any way.

Food Composition

The present disclosure provides a food composition for preventing or improving tuberculosis including a *Bacillus velezensis* PMC 206 strain. In particular, the food composition includes a health functional food composition, and although the health functional food is not particularly limited as long as it includes the *Bacillus velezensis* PMC 206 strain, the strain may be included in an amount of 0.01 wt % to 20 wt % based on the total weight of the health functional food composition.

In the food composition for preventing or improving tuberculosis according to the present disclosure, the food composition is not particularly limited as long as it is a food that is commonly prepared and/or sold. For example, the food composition includes meats, sausages, bread, chocolate, candies, snacks, confectionery, pizza, ramen, other noodles, gums, dairy products including ice creams, various kinds of soups, beverages, teas, drinks, alcoholic beverages, and vitamin complexes, which may be used in the form of pills, powders, granules, precipitates, tablets, capsules, or beverages, and the food composition includes all health functional foods in the conventional sense.

In the food composition for preventing or improving tuberculosis according to the present disclosure, the food composition has no particular limitation on liquid ingredients other than including the strain described above, it may include various kinds of flavoring agents or natural carbohydrates (e.g., as common beverages) as additional ingredients. Examples of carbohydrates include conventional sugars such as monosaccharides (e.g., glucose, fructose, etc.); disaccharides (e.g., maltose, sucrose, etc.); polysaccharides (e.g., dextrin, cyclodextrin); etc. and sugar alcohols (e.g., xylitol, sorbitol, erythritol, etc.). As flavoring agents other than those described above, natural flavoring agents (thaumatin, *stevia* extracts (e.g., rebaudioside A, glycyrrhizin, etc.)) and synthetic flavoring agents (saccharin, aspartame, etc.) may be advantageously used.

In the food composition for preventing or improving tuberculosis according to the present disclosure, the food composition may include, in addition to the additional ingredients described above, various kinds of nutrients, vitamins, minerals (electrolytes), flavoring agents (e.g. synthetic and natural flavoring agents), coloring agents and thickening agents (cheese, chocolate, etc.), pectic acid and salts thereof, alginic acid and salts thereof, organic acids, protective colloidal thickeners, pH adjusters, stabilizers, preservatives, glycerin, alcohol, carbonating agents used in carbonated drinks, etc.

Hereinafter, the present disclosure will be described in detail through examples. In particular, these examples are solely for describing the present disclosure more specifically, and it is obvious to those skilled in the art that the scope of the present disclosure is not limited by these examples.

<Experimental Methods>

1. Isolation, Identification, and Genetic Characterization of Probiotic Strain from Vinegar A probiotic strain was isolated from Korean traditional fermented vinegar and cultured in a food grade medium. The probiotic strain was cultured in a food-grade medium (glucose 20 g/L, yeast peptone standard-type F 25 g/L, Tween 80 1 g/L, magnesium sulfate 0.2 g/L, pH 6.3). The isolation, cultivation, and storage of the strain were performed as described in a previous report [Yoon Y, Seo H, Kim S, et al. Anti-Tuberculosis Activity of *Pediococcus acidilactici* Isolated from Young Radish Kimchi against *Mycobacterium tuberculosis*. J Microbiol Biotechnol. 2021 Dec. 28; 31(12): 1632-1642.]. The strain was confirmed by sequence analysis of 16s rRNA gene.

The sequencing of 16s rRNA gene was performed by Biofact (Korea) and was compared with the GenBank database using the basic local alignment search tool (BLAST) in the National Center for Biotechnology Information (NCBI). For the sequencing of the whole genome the strain, gDNA was extracted from the strain, sequenced using PacBio RSII (PacBio, USA) at CJ Bioscience (Korea), and analyzed with the Ezbiocloud server. The information of the genome of the *Bacillus beregensis* PMC206 strain was deposited on the NCBI website under Accession No. PRJNA865468.

2. In Vitro Antifungal Activity Test on Macrophages

Murine Raw 264.7 macrophages which have reached confluence were infected with *M. tuberculosis*, treated with probiotics or drugs according to the present disclosure, cultured for 3 days, and then CFU analysis was performed. H37Rv and XDR of the *Mycobacterium tuberculosis* strain used in this study were purchased from American Type Culture Collection (ATCC, USA) and Korean *Mycobacterium* Resource Center (KMRC, Korea), respectively. The synergistic effect of rifampicin (RIF) and isoniazid (INH), which are representative first-line drugs for the treatment of tuberculosis, was also examined.

3. Evaluation of In Vivo Anti-Tuberculosis Efficacy of Probiotics

The in vivo anti-tuberculosis effect of probiotics according to the present disclosure was evaluated in a mouse model of XDR pulmonary tuberculosis and a mouse model of latent tuberculosis. First, 6-week-old Balb/c mice were infected with the XDR strain by high-dose lung inhalation using a nebulizer, and were then administered with the probiotic strain by lung inhalation three times a day starting one week after infection. In a mouse model of latent pulmonary tuberculosis, mice were infected with a low-dose of the XDR strain, and one month thereafter, the mice were administered with the probiotic strain by lung inhalation once a day, twice a week for 8 months. Rifampicin was used as a control drug and was administered orally at 30 mg/kg. In this animal experiment, saline was used as a vehicle. For further analysis, lungs were extracted and *M. tuberculosis* was quantitatively analyzed by CFU and real-time PCR. Primers used were KY18 (forward, 5'-CACATGCAAGTCGAACGGAAAGG-3' (SEQ ID NO: 2); reverse, 5'-CCTTTCCGTTCGACTTGCATGTG-3' (SEQ ID NO: 3)) and KY75 (forward, 5'-GCCCGTATCGCCCGCACGCTCACA-3' (SEQ ID NO: 4); reverse, 5'-TGTGAGCGTGCGGGCGATACGGGC-3' (SEQ ID NO: 5)). Perfused lungs were used to examine the lung microenvironment in the mouse model of XDR pulmonary tuberculosis. Microbiome and metabolite analyses were performed according to previously reported methods. Lung cytokines were analyzed using a mouse ELISA kit (Thermo Fisher Scientific, USA), and the hematoxylin and eosin (H&E) staining analysis was performed in the Korea Pathology Technical Center (KPNT, Korea).

<Results>

1. Genetic Characterization of Probiotic Strain

A probiotic strain isolated from vinegar, a traditional fermented food, was identified based on the gene sequence of 16s rRNA and then confirmed by the analysis of the whole genome. As a result, it was found that the genome of the isolated probiotic strain consisted of a 3,990,015 bp single circular chromosome with 3,841 coding sequences (CDS) (FIG. 1A), and a total of 3,492 predicted proteins were grouped according to clusters of Orthologous Groups (COG) functional classification (FIG. 1B). As a result of similarity analysis using the Orthologous Average Nucleotide Identity (Ortho ANI) method, it was found that the similarity of the probiotic strain with *B. velezensis* was high, whereas the similarity of the probiotic strain with other *Bacillus* species appeared to be low; therefore, the probiotic strain isolated from vinegar was ultimately confirmed to be a *B. velezensis* strain (FIG. 1C). In addition, the isolated *Bacillus beregensis* variant was named PMC 206 as a novel strain that was genetically different from previously reported variants (FIG. 1D).

2. Evaluation of Antimycobacterial Activity of *Bacillus velezensis* PMC 206

The antimycobacterial activity of the *Bacillus velezensis* PMC 206 strain according to the present disclosure was confirmed using an in vitro macrophage infection model. Raw 264.7 cells were infected with the H37Rv strain, treated with the PMC 206 extract for 3 days, and then quantified through colony-forming unit (CFU) analysis. As a result, it was found that the PMC206 extract significantly inhibited both H37Rv (FIG. 2A) and XDR strains (FIG. 2B) at a concentration of 3.12 CFU/mL or higher. The tested INH and RIF showed significant effects at 1 μg/mL or 10 μg/mL against H37Rv, but they were shown to have an inhibitory effect only at a very high concentration of 100 μg/mL against XDR strains. Meanwhile, in the case of the XDR strain, PMC206 appeared to have a synergistic effect with 0.1 μg/mL RIF (FIG. 2C). Meanwhile, the concentration of PMC206, which does not exhibit cytotoxicity, was confirmed to be up to 6.25 CFU/mL (FIG. 2D).

Figure 3A:
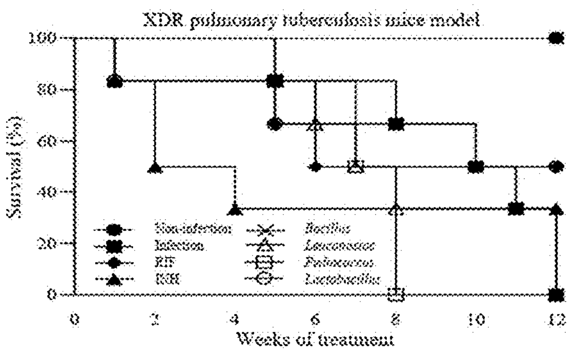
FIGS. 3A-3F shows the efficacy of the *Bacillus velegensis* PMC 206 strain according to the present disclosure in a fatal XDR pulmonary tuberculosis mouse model.
Figure 3B:
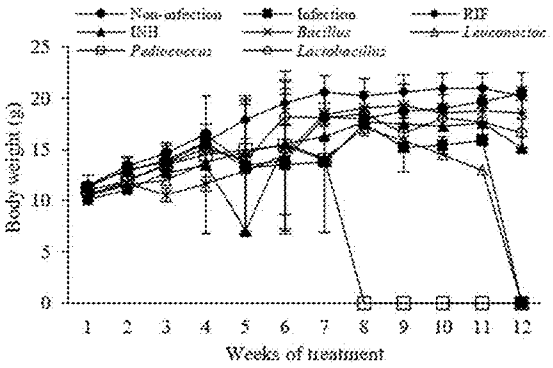
Figure 3C:
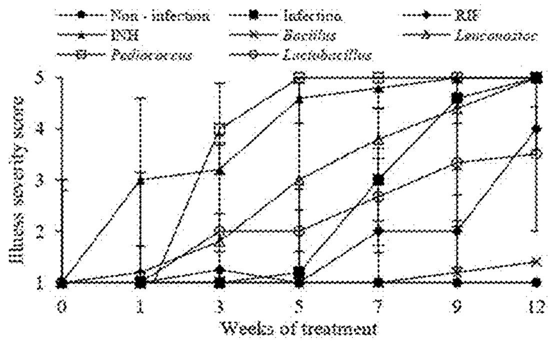
Figure 3D:
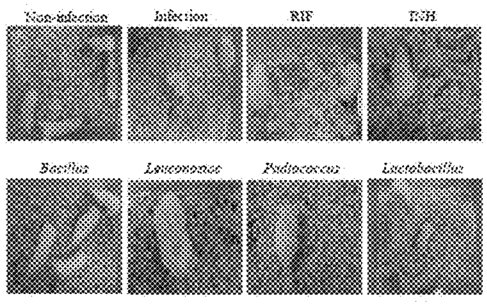
Figure 3E:
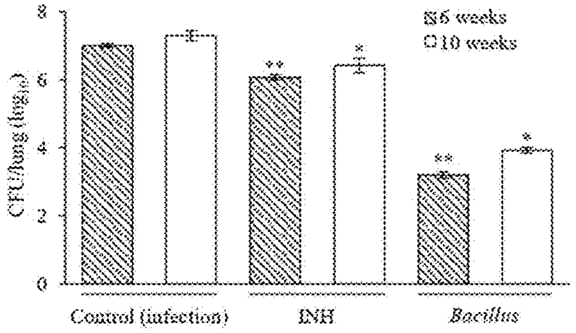
Figure 3F:
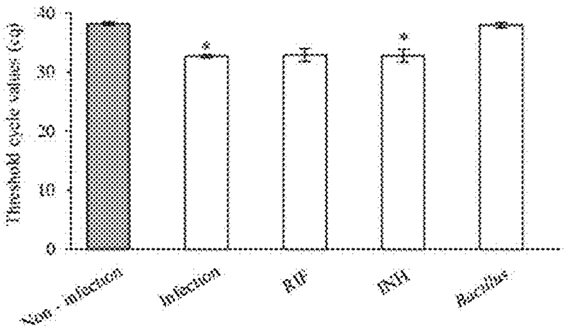

3. Evaluation of Efficacy of *Bacillus velezensis* PMC 206 in a Mouse Model of Fatal XDR Pulmonary Tuberculosis The in vivo efficacy of the *Bacillus velezensis* PMC 206 strain according to the present disclosure was evaluated using a mouse model of XDR pulmonary tuberculosis. Six-week-old Balb/c mice were infected with the XDR strain by high-dose lung inhalation using a nebulizer, and were then administered in the same manner with the *Bacillus velezensis* PMC 206 strain once a day and three times a week, and the mortality was observed. As a result, the infected mice died on the 12th week after the end of the experiment (FIG. 3A). All of the mice in groups administered with *Lactobacillus, Leuconostoc*, and *Pediococcus* also died. However, in the group administered with *Bacillus*, all mice survived until the end of the experiment. Meanwhile, the survival rates of mice in the INH group and RIF group were 16.6% and 32.2%, respectively. In relation to the above, it was confirmed that only the *Bacillus* group showed no significant weight loss compared to normal uninfected mice (FIG. 3B) and there was no significant difference in scores of disease severity (FIGS. 3C and 3D). Meanwhile, as a result of further analysis on the extracted lungs, it was found that the burden of *M. tuberculosis* in the lungs of mice treated with *Bacillus* was significantly reduced by Log 3.8 and Log 3.4 on the 6th week and the 10th week, respectively, compared to the control group (infected mice not treated with *Bacillus*) (FIG. 3E). This was confirmed to be consistent with the real-time PCR results using *M. tuberculosis* targeting primers (FIG. 3F).

Figure 4B:
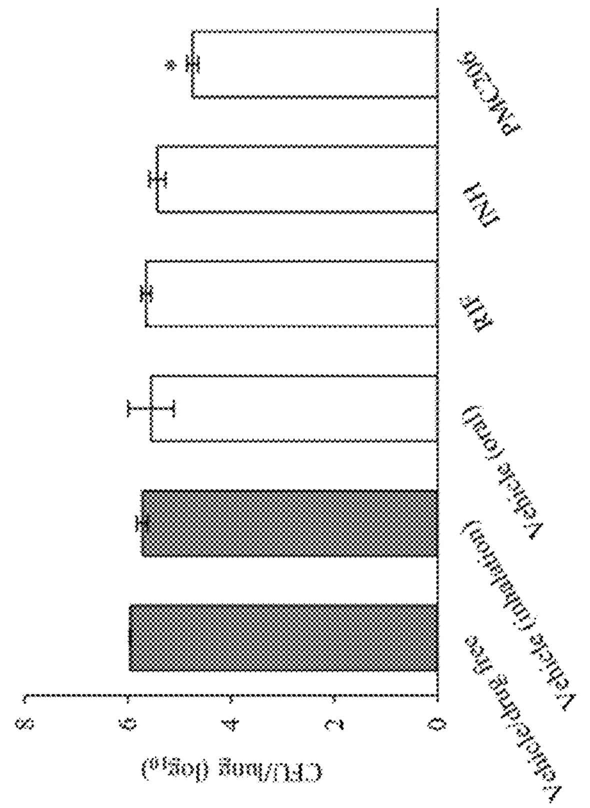
FIGS. 4A-4B shows the efficacy of the *Bacillus velegensis* PMC 206 strain according to the present disclosure in a latent tuberculosis mouse model.
Figure 4A:
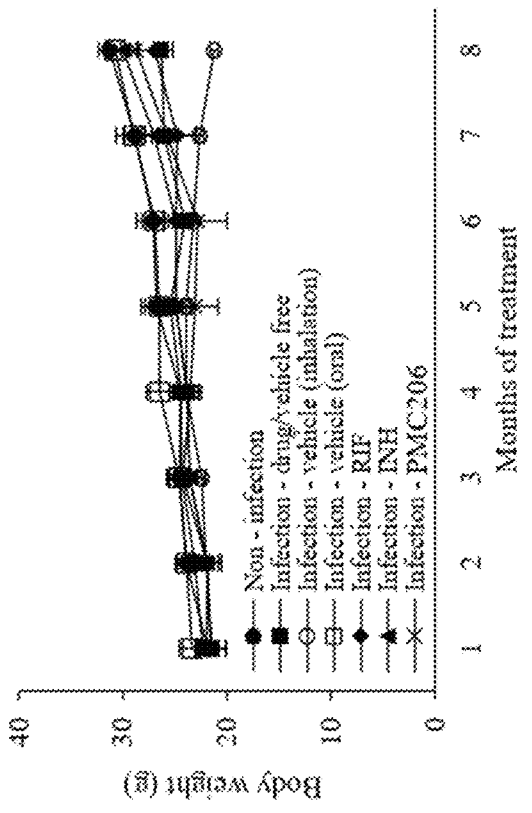

4. Evaluation of Efficacy of *Bacillus velezensis* PMC 206 in Mouse Model of Latent Tuberculosis As a result of evaluating the efficacy of the *Bacillus velezensis* PMC 206 strain in a model of latent tuberculosis induced by low-dose infection with the XDR strain, no significant change in body weight was observed upon administration of PMC206 (FIG. 4A), whereas the number of *Mycobacterium tuberculosis* bacteria in the lungs of mice was confirmed to decrease by about log 1.5 compared to that of the control group (FIG. 4B). Meanwhile, 30 mg/kg of INH also significantly reduced the number of *M. tuberculosis*, but the decrease caused by the administration of PMC206 was confirmed to be more significant. There was no significant difference in the groups administered with the same amount of RIF.

5. Analysis of Characteristics of Intrapulmonary Microenvironment in Treating *M. tuberculosis* by *Bacillus velezensis* PMC 206

Figure 5A:
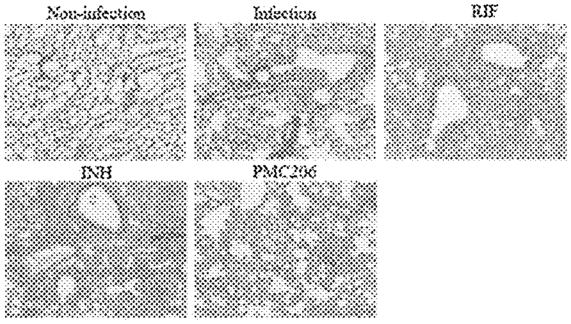
FIGS. 5A-5F shows the results of the lung immune response and pathology of the *Bacillus velegensis* PMC 206 strain according to the present disclosure.
Figure 5B:
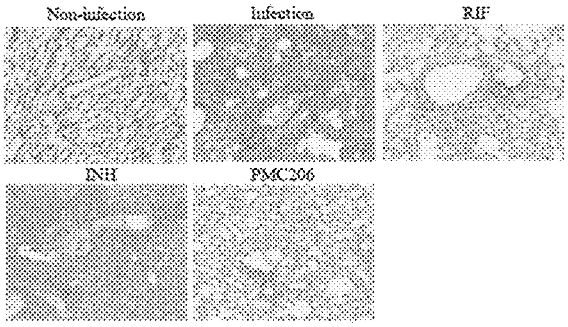
Figure 5C:
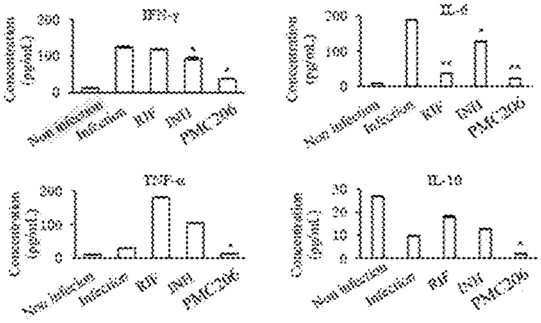
Figure 5D:
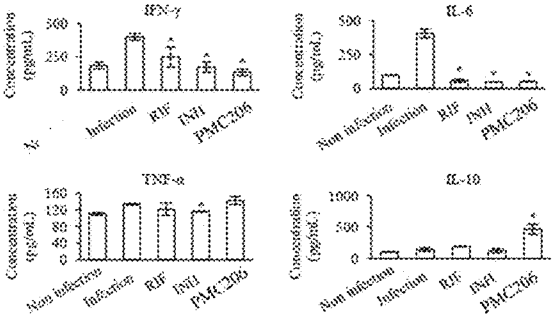
Figure 5E:
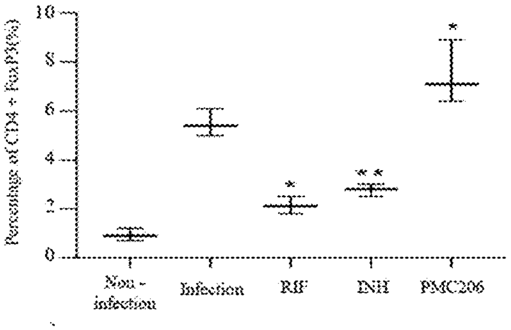
Figure 5F:
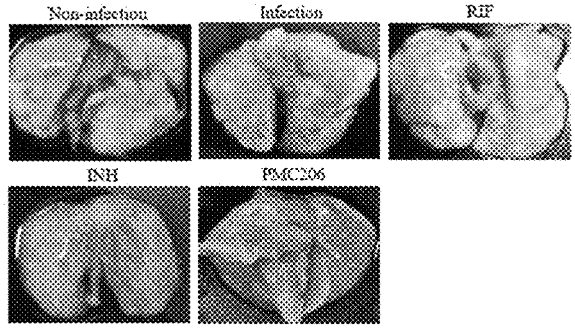

In order to examine the characteristics of the intrapulmonary microenvironment in treating *M. tuberculosis* by the *Bacillus velezensis* PMC 206 strain according to the present disclosure, granuloma formation and immune response analysis were performed. As a result, unlike in uninfected mice, granulomas were formed in the lungs of mice infected with *M. tuberculosis* in both models, and while relatively few granulomas were formed in PMC206-treated mice (FIGS. 5A and 5B), the lungs of mice administered with INH or RIF showed no significant reduction compared to the lungs of infected control mice. The quantitative analysis of cytokines in the lungs also showed similar trends in both models (FIGS. 5C and 5D). Overall, pro-inflammatory cytokines in the lungs of the mice treated with PMC206 were decreased compared to that of the infected control group, and the number of regulatory T cells was significantly increased by PMC206 (FIG. 5E). Additionally, the formation of granulomas was confirmed with the naked eye in the images of resected lungs, as described above (FIG. 5F).

Figure 6A:
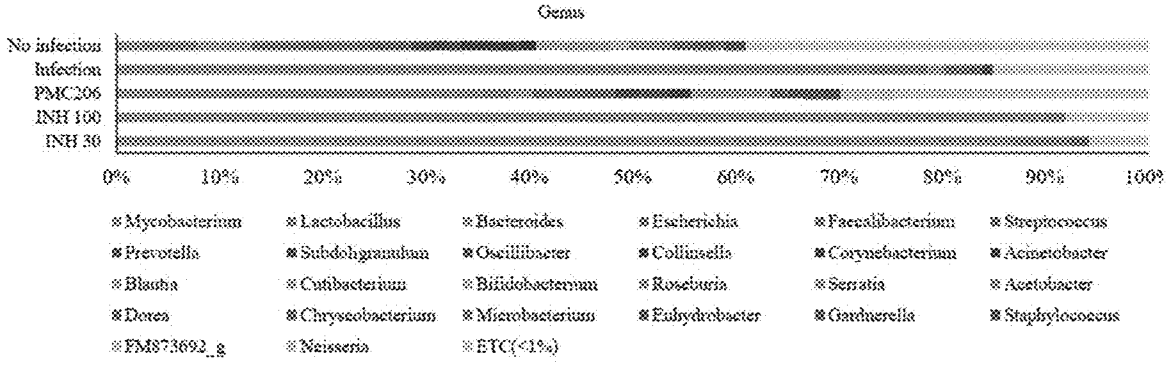
FIGS. 6A-6B shows the analysis of the lung microbial community microenvironment in a tuberculosis mouse model of the *Bacillus velegensis* PMC 206 strain according to the present disclosure.
Figure 6B:
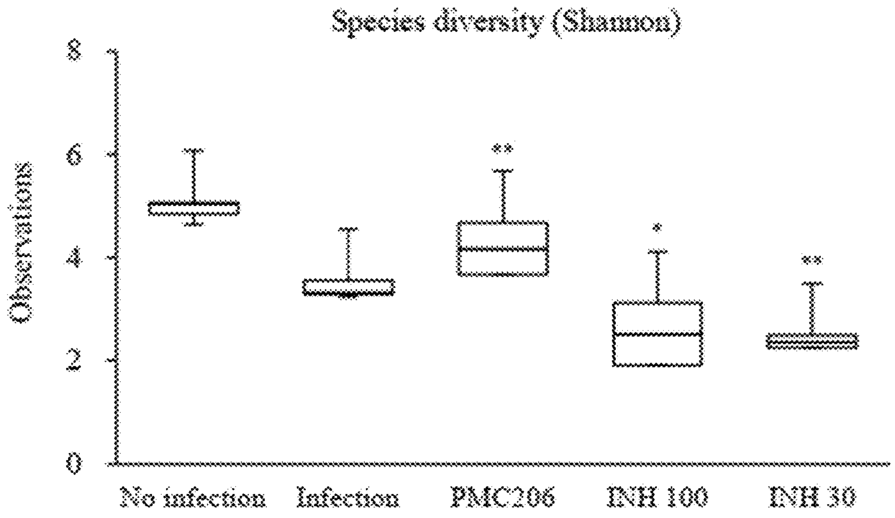

As a result of performing the analysis of 16S rRNA gene-based lung metagenomics in a mouse model of lethal pulmonary tuberculosis, while the occupancy of *M. tuberculosis* in the lungs of mice treated with PMC206 decreased compared to that of the infected control group, it did not decrease in the groups treated with INH or RIF (FIG. 6A). In the case of *Bacillus*, the detection rate was less than 1% and could not be expressed in the graph. More specifically, according to the Shanon-based alpha diversity analysis, when PMC206 was administered, the species diversity, which had been lowered due to infection, was significantly restored (FIG. 6B). However, it was confirmed that INH or RIF administration actually worsened the severity.

6. Effect of Autophagy Induction by *Bacillus velezensis* PMC 206

Figure 7A:
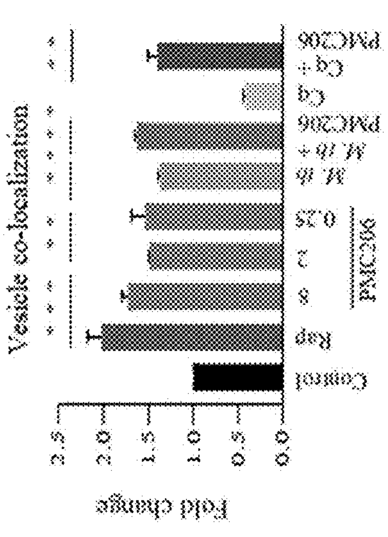
FIGS. 7A-7F shows the results of autophagy induction profiling in a tuberculosis mouse model of the *Bacillus velegensis* PMC 206 strain according to the present disclosure.
Figure 7B:
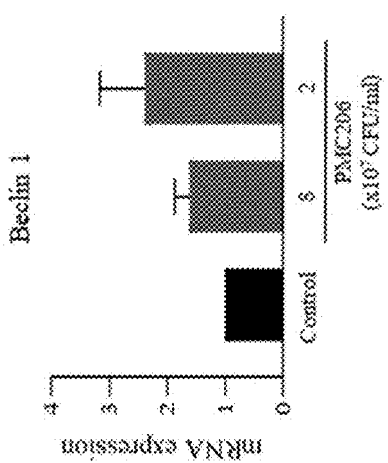
Figure 7C:
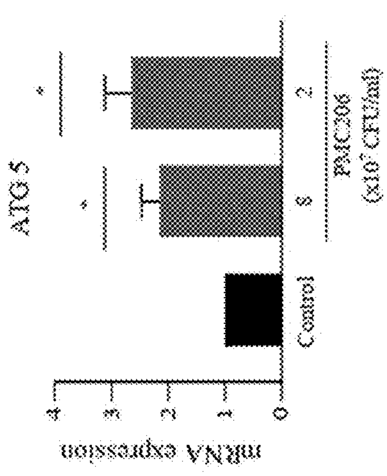
Figure 7D:
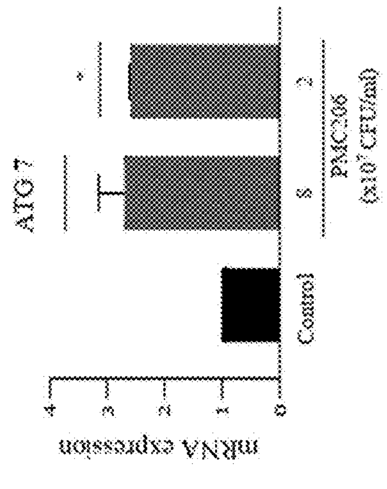
Figure 7E:
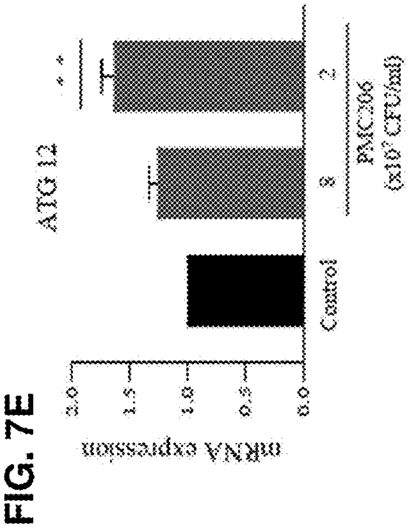
Figure 7F:
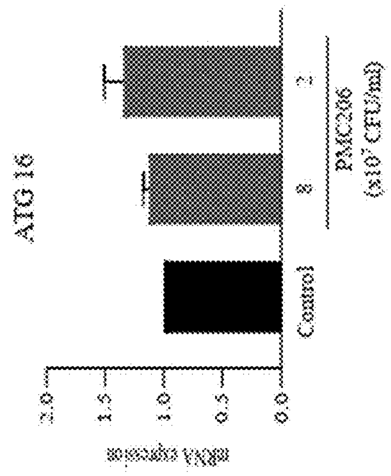

As a result of confirming the profiling regarding the induction of autophagy by PMC206 in a macrophage model infected with *M. tuberculosis*, PMC206 was shown to increase autophagic vacuoles in the model (FIG. 7A). It was also confirmed that PMC206 significantly upregulates the transcription of Beclin 1 and autophagy-related genes (ATG), which are known to play a central role in autophagy (FIGS. 7B to 7F).

Figure 8B:
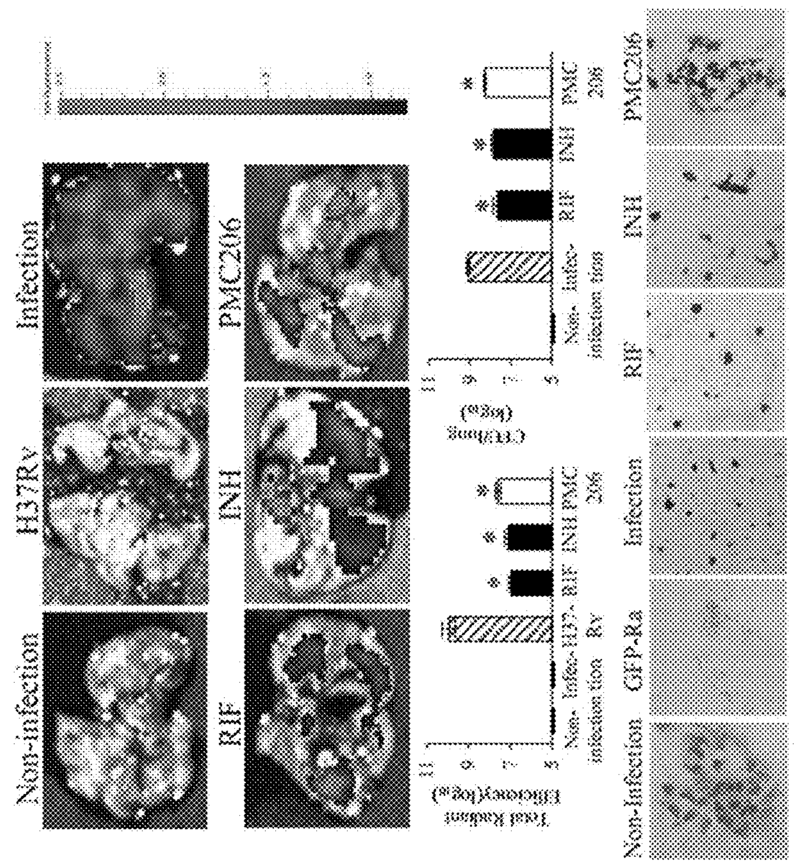
FIGS. 8A-8B shows the synergistic effect and preventive effect of the *Bacillus velegensis* PMC 206 strain according to the present disclosure.
Figure 8A:
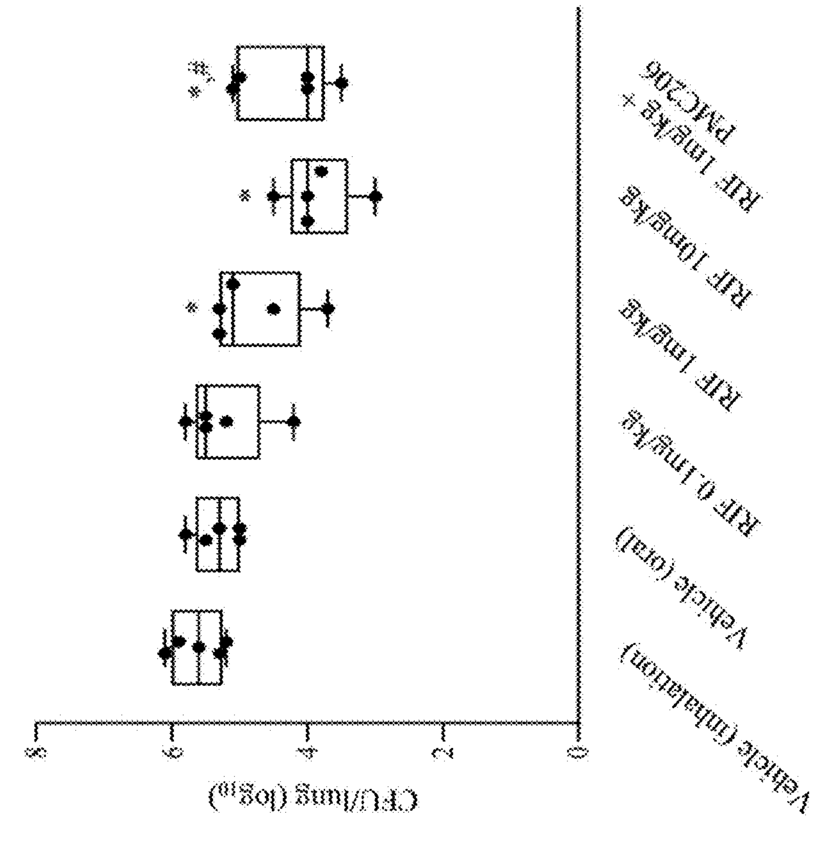

7. Synergistic and Preventive Effects of *Bacillus velezensis* PMC 206 on Pulmonary Tuberculosis As a result of confirming additional synergistic and preventive effects in a macrophage model infected with *M. tuberculosis*, it was confirmed that while RIF at 1 mg/kg/day did not significantly reduce the burden of *M. tuberculosis* in the lungs throughout the entire experiment, a significant reduction could be achieved when the same concentration of RIF and PMC206 were administered in combination (FIG. 8A). Additionally, as a result of confirming the preventive effect by administering probiotics 1 week before *M. tuberculosis* infection and up to 4 weeks after infection, the signals for fluorescent *M. tuberculosis* were shown to be significantly reduced in the lungs of mice administered with PMC206 (FIG. 8B).

As described above, specific parts of the present disclosure have been described in detail; however, it is obvious to those skilled in the art that these specific techniques are merely preferred exemplary embodiments and the scope of the present disclosure is not limited thereto. Accordingly, the actual scope of the present disclosure will be defined by the accompanying claims and equivalents thereof.

[Accession No.]

Depositary Authority: Korean Collection for Type Cultures

Accession No: KCTC15187BP

Date of Deposit: Nov. 9, 2022

Address of Depositary Authority: Korea Research Institute of Bioscience and Biotechnology 181, Ipsin-gil, Jeongeup-si, Jeollabuk-do 56212, Republic of Korea

```
16S rRNA sequence of KCTC15187BP
                                        (SEQ ID NO: 1)
GACGAACGCTGGCGGCGTGCCTAATACATGCAAGTCGAGCGGACAGATGG

GAGCTTGCTCCCTGATGTTAGCGGCGGACGGGTGAGTAACACGTGGGTAA

CCTGCCTGTAAGACTGGGATAACTCCGGGAAACCGGGGCTAATACCGGAT

GGTTGTTTGAACCGCATGGTTCAAACATAAAAGGTGGCTTCGGCTACCAC
```

-continued

TTACAGATGGACCCGCGGCGCATTAGCTAGTTGGTGAGGTAATGGCTCAC
CAAGGCAACGATGCGTAGCCGACCTGAGAGGGTGATCGGCCACACTGGGA
CTGAGACACGGCCCAGACTCCTACGGGAGGCAGCAGTAGGGAATCTTCCG
CAATGGACGAAAGTCTGACGGAGCAACGCCGCGTGAGTGATGAAGGTTTT
CGGATCGTAAAGCTCTGTTGTTAGGGAAGAACAAGTACCGTTCGAATAGG
GCGGTACCTTGACGGTACCTAACCAGAAAGCCACGGCTAACTACGTGCCA
GCAGCCGCGGTAATACGTAGGTGGCAAGCGTTGTCCGGAATTATTGGGCG
TAAAGGGCTCGCAGGCGGTTTCCTTAAGTCTGATGTGAAAGCCCCCGGCT
CAACCGGGGAGGGTCATTGGAAACTGGGGAACTTGAGTGCAGAAGAGGAG
AGTGGAATTCCACGTGTAGCGGTGAAATGCGTAGAGATGTGGAGGAACAC
CAGTGGCGAAGGCGACTCTCTGGTCTGTAACTGACGCTGAGGAGCGAAAG
CGTGGGGAGCGAACAGGATTAGATACCCTGGTAGTCCACGCCGTAAACGA
TGAGTGCTAAGTGTTAGGGGGTTTCCGCCCCTTAGTGCTGCAGCTAACGC

-continued

ATTAAGCACTCCGCCTGGGGAGTACGGTCGCAAGACTGAAACTCAAAGGA
ATTGACGGGGGCCCGCACAAGCGGTGGAGCATGTGGTTTAATTCGAAGCA
ACGCGAAGAACCTTACCAGGTCTTGACATCCTCTGACAATCCTAGAGATA
GGACGTCCCCTTCGGGGGCAGAGTGACAGGTGGTGCATGGTTGTCGTCAG
CTCGTGTCGTGAGATGTTGGGTTAAGTCCCGCAACGAGCGCAACCCTTGA
TCTTAGTTGCCAGCATTCAGTTGGGCACTCTAAGGTGACTGCCGGTGACA
AACCGGAGGAAGGTGGGGATGACGTCAAATCATCATGCCCCTTATGACCT
GGGCTACACACGTGCTACAATGGACAGAACAAAGGGCAGCGAAACCGCGA
GGTTAAGCCAATCCCACAAATCTGTTCTCAGTTCGGATCGCAGTCTGCAA
CTCGACTGCGTGAAGCTGGAATCGCTAGTAATCGCGGATCAGCATGCCGC
GGTGAATACGTTCCCGGGCCTTGTACACACCGCCCGTCACACCACGAGAG
TTTGTAACACCCGAAGTCGGTGAGGTAACCTTTTAGGAGCCAGCCGCCGA
AGGTGGGACAGATGATTG

What is claimed is:

1. A pharmaceutical composition for treating tuberculosis having antibacterial activity against *Mycobacterium tuberculosis*, comprising the *Bacillus velezensis* PMC 206 strain or a culture thereof as an active ingredient, wherein the strain has the 16S rRNA sequence of SEQ ID NO:1, wherein the strain is deposited with the Korean Collection for Type Cultures (KCTC) under Accession No. KCTC 15187BP.

2. The pharmaceutical composition of claim 1, wherein the tuberculosis comprises one or more selected from the group consisting of ocular tuberculosis, skin tuberculosis, adrenal tuberculosis, renal tuberculosis, epididymal tuberculosis, lymphatic tuberculosis, laryngeal tuberculosis, middle ear tuberculosis, intestinal tuberculosis, multidrug-resistant tuberculosis, pulmonary tuberculosis, biliary tuberculosis, bone tuberculosis, throat tuberculosis, breast tuberculosis, and spinal tuberculosis.

3. The pharmaceutical composition of claim 1, wherein the tuberculosis is latent tuberculosis.

4. The pharmaceutical composition of claim 1, wherein the pharmaceutical composition further comprises at least one selected from the group consisting of rifampicin, rifapentine, isoniazid, pyrazinamide, ethambutol, streptomycin, fluoroquinolone, kanamycin, cycloserine, prothionamide, levofloxacin, moxifloxacin, ofloxacin, rifabutin, capeomycin, amikacin, ciprofloxacin, protionamide, ethionamide, cycloserine, thioacetazone, clofazimine, amoxicillin/clavulanate, a derivative of dianomidiphenylsulphone, clarithromycin, azithromycin, and linezolid.

5. A food composition for treating tuberculosis having antibacterial activity against *Mycobacterium tuberculosis*, comprising the *Bacillus velezensis* PMC 206 strain or a culture thereof as an active ingredient, wherein the strain has the 16S rRNA sequence of SEQ ID NO:1, wherein the strain is deposited with the Korean Collection for Type Cultures (KCTC) under Accession No. KCTC 15187BP.

6. The food composition of claim 5, wherein the tuberculosis comprises one or more selected from the group consisting of ocular tuberculosis, skin tuberculosis, adrenal tuberculosis, renal tuberculosis, epididymal tuberculosis, lymphatic tuberculosis, laryngeal tuberculosis, middle ear tuberculosis, intestinal tuberculosis, multidrug-resistant tuberculosis, pulmonary tuberculosis, biliary tuberculosis, bone tuberculosis, throat tuberculosis, breast tuberculosis, and spinal tuberculosis.

7. The food composition of claim 5, wherein the tuberculosis is latent tuberculosis.

* * * * *

SEQUENCE LISTING

```
Sequence total quantity: 5
SEQ ID NO: 1            moltype = DNA  length = 1468
FEATURE                 Location/Qualifiers
source                  1..1468
                        mol_type = other DNA
                        organism = synthetic construct
SEQUENCE: 1
gacgaacgct ggcggcgtgc ctaatacatg caagtcgagc ggacagatgg gagcttgctc  60
cctgatgtta gcggcggacg ggtgagtaac acgtgggtaa cctgcctgta agactgggat  120
aactccggga aaccggggct aataccggat ggttgtttga accgcatggt tcaaacataa  180
aaggtggctt cggctaccac ttacagatgg acccgcggcg cattagctag ttggtgaggt  240
aatggctcac caaggcaacg atgcgtagcc gacctgagag ggtgatcggc cacactggga  300
ctgagacacg gcccagactc ctacgggagg cagcagtagg gaatcttccg caatggacga  360
aagtctgacg gagcaacgcc gcgtgagtga tgaaggtttt cggatcgtaa agctctgttg  420
ttagggaaga acaagtaccg ttcgaatagg gcggtacctt gacggtacct aaccagaaag  480
ccacggctaa ctacgtgcca gcagccgcgg taatacgtag gtggcaagcg ttgtccggaa  540
ttattgggcg taaagggctc gcaggcggtt tccttaagtc tgatgtgaaa gcccccggct  600
caaccgggga gggtcattgg aaactgggga acttgagtgc agaagaggag agtggaattc  660
cacgtgtagc ggtgaaatgc gtagagatgt ggaggaacac cagtggcgaa ggcgactctc  720
tggtctgtaa ctgacgctga ggagcgaaag cgtggggagc gaacaggatt agataccctg  780
gtagtccacg ccgtaaacga tgagtgctaa gtgttagggg gtttccgccc cttagtgctg  840
cagctaacgc attaagcact ccgcctgggg agtacggtcg caagactgaa actcaaagga  900
attgacgggg gcccgcacaa gcggtggagc atgtggttta attcgaagca acgcgaagaa  960
ccttaccagg tcttgacatc ctctgacaat cctagagata ggacgtcccc ttcgggggca  1020
gagtgacagg tggtgcatgg ttgtcgtcag ctcgtgtcgt gagatgttgg gttaagtccc  1080
gcaacgagcg caacccttga tcttagttgc cagcattcag ttgggcactc taaggtgact  1140
gccggtgaca aaccggagga aggtggggat gacgtcaaat catcatgccc cttatgacct  1200
gggctacaca cgtgctacaa tggacagaac aaagggcagc gaaaccgcga ggttaagcca  1260
atcccacaaa tctgttctca gttcggatcg cagtctgcaa ctcgactgcg tgaagctgga  1320
atcgctagta atcgcggatc agcatgccgc ggtgaatacg ttcccgggcc ttgtacacac  1380
cgcccgtcac accacgagag tttgtaacac ccgaagtcgg tgaggtaacc ttttaggagc  1440
cagccgccga aggtgggaca gatgattg                                     1468

SEQ ID NO: 2            moltype = DNA  length = 23
FEATURE                 Location/Qualifiers
source                  1..23
                        mol_type = other DNA
                        organism = synthetic construct
SEQUENCE: 2
cacatgcaag tcgaacggaa agg                                          23

SEQ ID NO: 3            moltype = DNA  length = 23
FEATURE                 Location/Qualifiers
source                  1..23
                        mol_type = other DNA
                        organism = synthetic construct
SEQUENCE: 3
cctttccgtt cgacttgcat gtg                                          23
```

-continued

```
SEQ ID NO: 4            moltype = DNA  length = 24
FEATURE                 Location/Qualifiers
source                  1..24
                        mol_type = other DNA
                        organism = synthetic construct
SEQUENCE: 4
gccccgtatcg cccgcacgct caca                                          24

SEQ ID NO: 5            moltype = DNA  length = 24
FEATURE                 Location/Qualifiers
source                  1..24
                        mol_type = other DNA
                        organism = synthetic construct
SEQUENCE: 5
tgtgagcgtg cgggcgatac gggc                                           24
```